April 28, 1964 C. FISCHER Plant Pat. 2,394
GLADIOLUS PLANT
Filed April 30, 1963
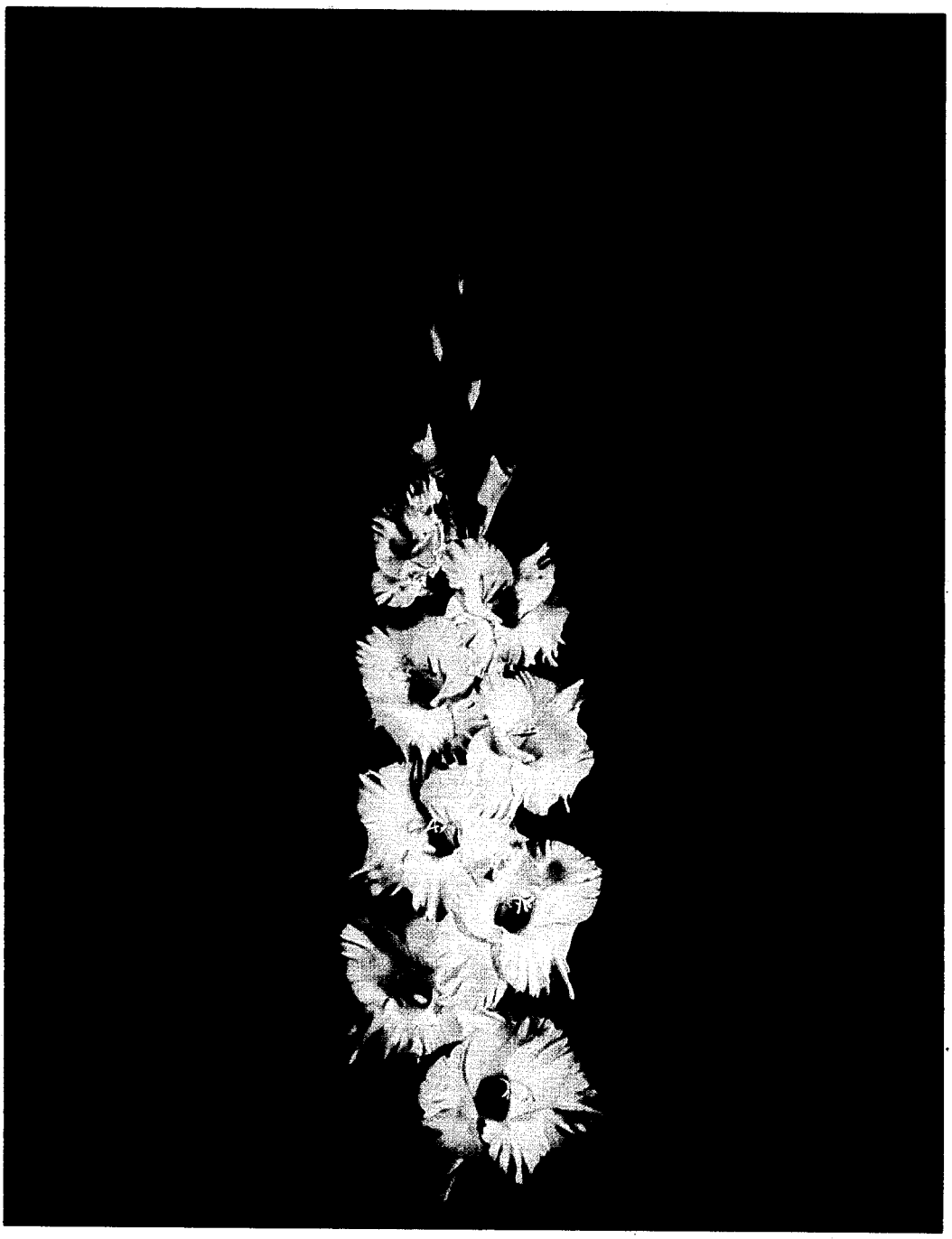
Inventor.
Carl Fischer
By: Robb & Robb
Attorneys United States Patent Office Plant Pat. 2,394
Patented Apr. 28, 1964

2,394
GLADIOLUS PLANT

Carl Fischer, St. Charles, Minn., assignor to Imperial Flowers Limited, Leamington, Ontario, Canada, a corporation of Ontario, Canada Filed Apr. 30, 1963, Ser. No. 277,052
1 Claim. (Cl. Plt.—85)

The present invention relates to a new and distinct variety of gladiolus plant which was originated by me by crossing the variety "Prospector" (unpatented) with an unnamed and unpatented gladiolus variety of unidentified origin, the former being the seed parent, and the latter being the pollen parent.

As the result of this breeding, I have produced a new and improved gladiolus variety, as evidenced by the following unique combination of characteristics which are outstanding therein and which distinguish it from its parents, as well as from all other varieties of which I am aware:

(1) An early blooming habit;
(2) Large flower size;
(3) A distinctive and attractive flower form; and
(4) A distinctive and attractive Carmine Rose general color tonality of the flowers, with the lip petal being creamy white and having a tint of pink on the edges after the flowers mature from opening buds which have a yellow tint in their Carmine Rose color.

My new variety resembles the variety known as "Innocence" (unpatented) more than any other variety, but differs therefrom particularly by an earlier blooming habit; larger flower size; more colorful, and hence more attractive flowers; and a heavier flower substance.

Asexual reproduction of my new variety by cormels through several generations, as performed by me at St. Charles, Minnesota, shows that the foregoing characteristics and distinctions come true to form and are established and transmitted through succeeding propagations.

The accompanying drawing shows a typical specimen flower spike of my new variety, with the flowers in different stages of development ranging from closed buds through partially open buds to fully open flowers, as depicted in color as nearly true as it is reasonably possible to make the same in a color illustration of this character.

The following is a detailed description of my new variety, with color terminology in accordance with the Horticultural Colour Charts issued by the British Colour Council and the Royal Horticultural Society, except where general color terms of ordinary dictionary significance are obvious:

Locality where grown and observed: St. Charles, Minnesota.

Propagation: Holds its distinguishing characteristics through succeeding propagations from cormels.

*Plant*

Growth: Vigorous grower; excellent propagator.

Blooming habit: Early; comes into bloom from the planting of large bulbs in about 65 days in the Northern latitudes of the United States.

Stems: Strong; straight.
*Diameter at base.*—About ½ inch.
*Color (at base).*—Light purple.

Foliage: Slightly drooping; leaves range from about 1⅞ inches to 2 inches wide and attain height of about 32 inches. Color—deep green.

Disease resistance: Average resistance to the usual diseases to which gladiolus varieties are subject, as determined by comparison with other varieties grown in my fields near St. Charles, Minnesota.

Corms (bulbs): Large; old corms have a rather rough appearance and tough husk of purple color; corms from young stock are smooth and clean. Color of flesh—Amber Yellow, Plate 505/1, with a tint of pink.

*Flower*

Spike: Blossom spike attains height of about 58 inches to 60 inches, with flower head being about 28 inches to 30 inches long; bears from 20 to 24 buds, with 7 or 8 buds open at one time.

Bud:
*Size.*—About 3 inches long when opening.
*Opening.*—7 or 8 buds show color at one time; average opening qualities from tight bud.

Flower:
*Arrangement.*—Florets are informally arranged on the stem.
*Size.*—Individual florets range from about 5½ inches to 6 inches in diameter.
*Form.*—Florets are round and ruffled.
*Keeping qualities.*—Average keeper.

Petals:
*Shape.*—Round; ruffled.
*Size.*—Upper petals—about 3 inches wide. Lip petal—about 2¼ inches wide.
*Aspect.*—Extremely heavy substance; surface has leathery texture.
*Fragrance.*—None.
*Color.*—Ranging from Carmine Rose, Plate 621/2 at the deepest shading to Carmine Rose, Plate 621/3, with general color tonality being Carmine Rose, Plate 621/3; lip petal is creamy white, with a tint of pink on the edges in the mature flowers after opening from Carmine Rose buds having a yellow tint.

*Reproductive Organs*

Stamens: Color—purple.
Pistil: Color—light pink.

I claim:

A new and distinct variety of gladiolus plant, substantially as herein shown and described, characterized particularly as to novelty by the unique combination of an early blooming habit, large flower size, a distinctive and attractive ruffled flower form, and a distinctive and attractive Carmine Rose general color tonality of the flowers, with the lip petals being creamy white and having a tint of pink on their edges after opening from Carmine Rose buds having a yellow tint.

No references cited.